US010561157B2

(12) United States Patent
Dörr et al.

(10) Patent No.: US 10,561,157 B2
(45) Date of Patent: Feb. 18, 2020

(54) ROLLING COMPOUND POWDERS FOR APPLYING ON THE SURFACE OF CHEWING GUM CORE MATERIALS

(71) Applicant: SUDZUCKER AKTIENGESELLSCHAFT MANNHEIM/OCHSENFURT, Mannheim (DE)

(72) Inventors: Tillmann Dörr, Hohen-Sülzen (DE); Jörg Bernard, Albsheim (DE)

(73) Assignee: SUDZUCKER AKTIENGESELLSCHAFT MANNHEIM/OCHSENFURT, Mannheim (DE)

( * ) Notice: Subject to any disclaimer, the term of this patent is extended or adjusted under 35 U.S.C. 154(b) by 0 days.

(21) Appl. No.: 14/387,057

(22) PCT Filed: Mar. 7, 2013

(86) PCT No.: PCT/EP2013/054601
§ 371 (c)(1),
(2) Date: Sep. 22, 2014

(87) PCT Pub. No.: WO2013/143823
PCT Pub. Date: Oct. 3, 2013

(65) Prior Publication Data
US 2015/0079227 A1    Mar. 19, 2015

Related U.S. Application Data

(60) Provisional application No. 61/618,011, filed on Mar. 30, 2012.

(30) Foreign Application Priority Data

Mar. 30, 2012 (EP) .................... 12002365

(51) Int. Cl.
A23G 4/20 (2006.01)
A23G 4/02 (2006.01)
(Continued)

(52) U.S. Cl.
CPC ................. *A23G 4/20* (2013.01); *A23G 4/00* (2013.01); *A23G 4/025* (2013.01); *A23G 4/06* (2013.01);
(Continued)

(58) Field of Classification Search
CPC . A23G 4/00; A23G 4/06; A23G 4/025; A23G 4/062; A23G 4/20; A23G 2200/06; C07H 3/04; A23L 1/09; A23V 2002/00
(Continued)

(56) References Cited

U.S. PATENT DOCUMENTS 4,976,972 A    12/1990  Patel et al.
4,988,518 A *  1/1991  Patel ........................ A23G 4/06
                                                    426/103
(Continued)

FOREIGN PATENT DOCUMENTS

CN      1076590 A       9/1993
WO      92/22217 A1    12/1992
(Continued)

OTHER PUBLICATIONS

Chinese Office Action for corresponding application CN 201380017265. 6, issued as CN 2015081701325250, with English translation thereof.
(Continued)

*Primary Examiner* — Subbalakshmi Prakash
(74) *Attorney, Agent, or Firm* — Stephen T. Olson; Harness, Dickey & Pierce, P.L.C.

(57) ABSTRACT

The present invention relates to rolling compound powders comprising hydrogenated or non-hydrogenated isomaltulose for applying to the surface of chewing gum core materials,
(Continued)

chewing gum products comprising such rolling compound powders, processes for reducing the stickiness of compositions of chewing gum core materials by using hydrogenated or non-hydrogenated isomaltulose-containing rolling compound powders in chewing gum preparation processes as well as the use of hydrogenated or non-hydrogenated isomaltulose in rolling compound powders for applying to the surface of chewing gum core materials.

19 Claims, 1 Drawing Sheet

(51) Int. Cl.
| | |
|---|---|
| A23G 4/06 | (2006.01) |
| A23G 4/00 | (2006.01) |
| A23L 29/30 | (2016.01) |
| C07H 3/04 | (2006.01) |

(52) U.S. Cl.
CPC .............. *A23G 4/062* (2013.01); *A23L 29/30* (2016.08); *C07H 3/04* (2013.01); *A23V 2002/00* (2013.01)

(58) Field of Classification Search
USPC .............................. 426/4, 658, 661; 536/123
See application file for complete search history.

(56) References Cited

U.S. PATENT DOCUMENTS

| | | | |
|---|---|---|---|
| 5,206,042 A | 4/1993 | Dave et al. | |
| 5,248,508 A | 9/1993 | Reed et al. | |
| 5,399,365 A | 3/1995 | Yatka et al. | |
| 5,494,685 A | 2/1996 | Tyrpin et al. | |
| 2005/0238777 A1 | 10/2005 | Klingeberg et al. | |
| 2009/0142444 A1* | 6/2009 | Jarrard, Jr. ........... | A23G 3/0085 426/5 |
| 2010/0316759 A1 | 12/2010 | Kowalczyk et al. | |
| 2011/0052756 A1 | 3/2011 | Cervenka et al. | |

FOREIGN PATENT DOCUMENTS

| | | |
|---|---|---|
| WO | 95/08926 A1 | 4/1995 |
| WO | 2009/021613 A1 | 2/2009 |
| WO | 2009/037319 A2 | 3/2009 |

OTHER PUBLICATIONS

Takada, Kenta, "Development and Application of Palatinit for Coating", Up-to-Date Food Processing, 1999, vol. 34, pp. 43-46, Japan.

Nagai, Yukie, et al., "Functionality of Reduced Palatinose® and the Field of Application Thereof", Japan Food Science, 2010, vol. 49, pp. 58-65, Japan.

Office Action dated Apr. 26, 2016, of the Japanese Patent Application No. 2015-502181, which corresponds to the above-identified application.

Office Action dated May 31, 2016 of the EP Application No. 13707672.5-1358, which corresponds to the above-identified application.

Office Action regarding JP Patent Application No. 2015-502181, dated Nov. 22, 2016 (with translation).

International Search Report and Written Opinion of the ISA for PCT/EP2013/054601, ISA/EP, Rijswijk, NL, dated Apr. 8, 2013.

Bolhuis, Gerad K. et al., "Compaction properties of isomalt." European Journal of Pharmaceutics and Biopharmaceutics, vol. 72, pp. 621-625 (2009).

* cited by examiner

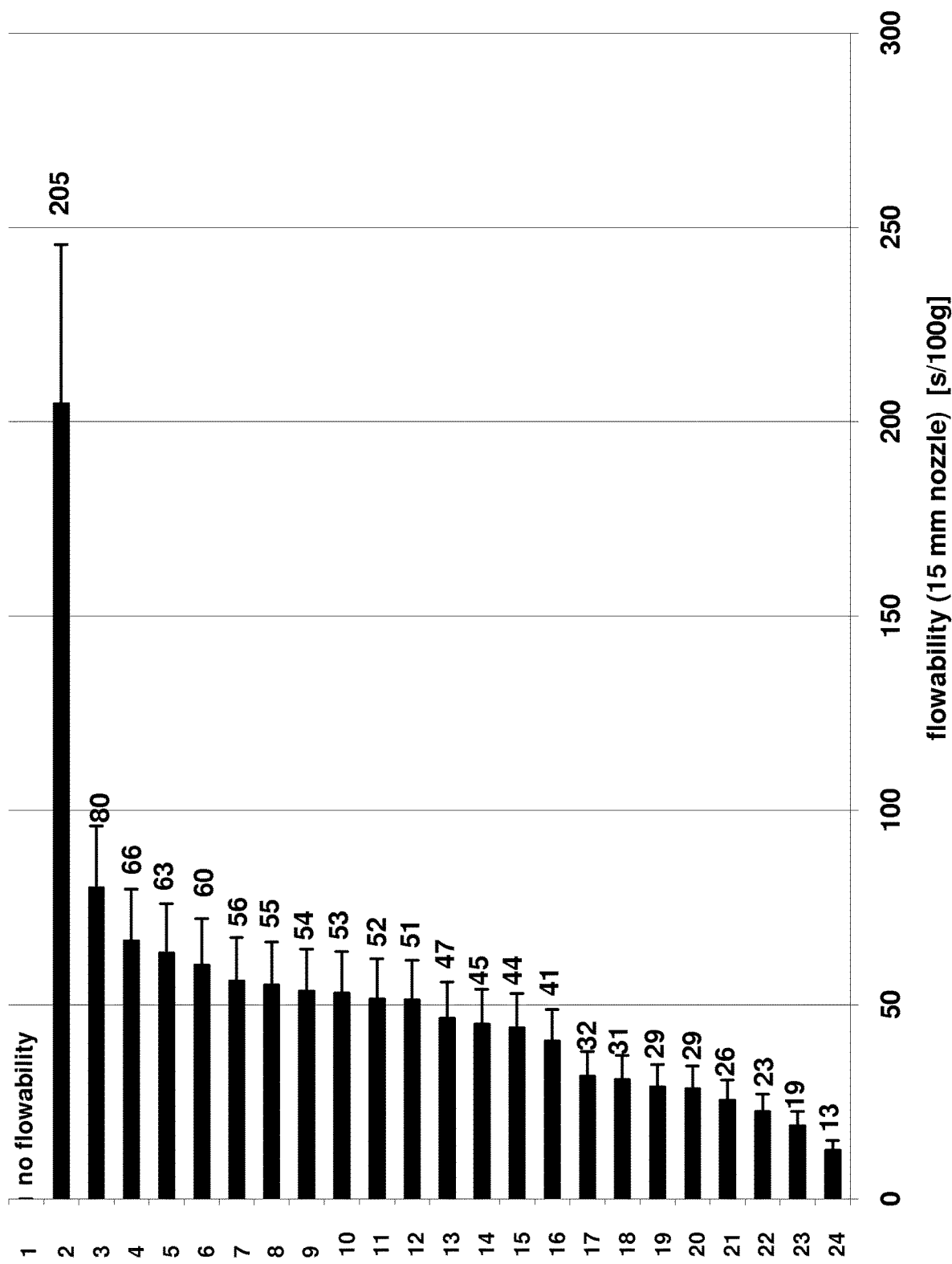

ROLLING COMPOUND POWDERS FOR APPLYING ON THE SURFACE OF CHEWING GUM CORE MATERIALS

CROSS-REFERENCE TO RELATED APPLICATIONS

This application is a 371 U.S. National Stage of International Application No. PCT/EP2013/054601, filed Mar. 7, 2013. This application claims priority to European Patent Application No. 12002365.0, filed Mar. 30, 2012 and claims the benefit of U.S. Provisional Application No. 61/618,011, filed Mar. 30, 2012. The entire disclosures of the above applications are incorporated herein by reference.

The present invention relates to rolling compound powders comprising hydrogenated or non-hydrogenated isomaltulose (isomaltulose is sold under the trademark PALATINOSE) for applying to the surface of chewing gum core materials, chewing gum products comprising such rolling compound powders, processes for reducing the stickiness of compositions of chewing gum core materials by using hydrogenated or non-hydrogenated isomaltulose-containing rolling compound powders in chewing gum preparation processes as well as the use of hydrogenated or non-hydrogenated isomaltulose in rolling compound powders for applying to the surface of chewing gum core materials.

It is known to dust products such as chewing gum and chewing gum cores with material such as powdered sugar to improve appearance and initial taste. The dusting also is intended to prevent the chewing gum from sticking to the fingers when handled or to the wrapper when the product is unwrapped.

However, the primary function of dusting compounds for chewing gum core materials is to make the chewing gum core more manageable during processing, including rolling. Dusting compounds used for this purpose are called rolling compounds.

A rolling compound is a powdery material used as a functional release agent between chewing gums or chewing gum cores and facility components and packaging. The rolling compound is applied to a sheet of chewing gum material or chewing gum core material as it moves through the machinery so to prevent adhesion of the chewing gum material or chewing gum core material to the machinery.

Conventional known rolling compounds include sucrose, mannitol, sorbitol, starch, calcium carbonate and talc. Sucrose is a sugar and therefore cannot be used in a sugar-less gum. Mannitol is today the most common sugar-less rolling compound, but it does not enhance initial sweetness of the chewing gum. Sorbitol can cause a burning sensation in the throat. Starch can give a dry mouth feel and can cause embrittlement of the gum by drawing water out of the gum stick. Calcium carbonate and talc can lead to negative sensorial effects. Currently still in most productions 100% talc or a combination of mannitol and talc is used as rolling compound.

U.S. Pat. No. 4,976,972 discloses a chewing gum composition with improved sweetness employing a xylitol rolling compound. U.S. Pat. No. 5,206,042 discloses a blend of mannitol and sorbitol used as a rolling compound. U.S. Pat. No. 5,494,685 discloses a chewing gum composition with a rolling compound containing erythritol and an anti-caking agent such as talc.

US 2011/0052756 A1 discloses the use of cooling energy instead of a rolling compound to prevent the adhesion of a chewing gum sheet to the machinery. However, this makes the machinery very complex and needs a lot of energy for cooling thereby increasing the costs.

The technical problem underlying the present invention is to provide rolling compounds having a good flowability. A further technical problem underlying the present invention is to provide rolling compounds having improved adhesion prevention.

A further technical problem underlying the present invention is to provide rolling compounds with improved sensory and taste profiles.

Furthermore, the rolling compounds should have preferably a low hygroscopicity and should be preferably cheap.

The present invention solves the underlying technical problem by the provision of a rolling compound powder for applying to the surface of a chewing gum core material, wherein the rolling compound powder comprises hydrogenated and/or non-hydrogenated isomaltulose.

In the context of the present invention a rolling compound is applied to or on the surface of a chewing gum core material. Accordingly a chewing gum core material has a rolling compound on its surface.

In a preferred embodiment of the present invention, the rolling compound powder comprises essentially hydrogenated or non-hydrogenated isomaltulose.

In the context of the present invention the term "comprising" preferably has the meaning of "containing" or "including" meaning that the composition in question at least comprises the specifically identified component without excluding the presence of further components. However, in a preferred embodiment the term comprising is also understood to have the meaning of "consisting essentially of" and in a most preferred embodiment of "consisting". The term "consisting essentially of" excludes the presence of substantial amounts of further components except the specifically identified component of the composition. The term "consisting" excludes the presence of any further compound, no matter in which quantity in the composition identified.

In the context of the present invention the term "comprising essentially" preferably has the meaning that the specifically identified component is the component with the highest proportion in the composition in question compared to the components present in the composition in question. However, in a preferred embodiment the term "comprising essentially" means that the composition in question comprises at least 50% by weight, even more preferably at least 51% by weight of the specifically identified component.

If not outlined else, %-values given the in present description mean weight-% on dry matter.

In the context of the present invention the term "at least one" preferably has the meaning that one component or more than one components, for example two, three or more components are present.

Surprisingly, it could be shown that rolling compound powders comprising hydrogenated or non-hydrogenated isomaltulose have a better flowability compared to mannitol based rolling compound powders. Furthermore the rolling compound powders according to the present invention are a good release agent, i.e they give good adhesion prevention. The rolling compound powders according to the present invention show also an improved sensory profile and give a good initial sweetness of the chewing gum.

In a preferred embodiment of the present invention, the rolling compound powder comprises hydrogenated or non-hydrogenated isomaltulose.

In a preferred embodiment of the present invention, the rolling compound powder comprises hydrogenated and non-hydrogenated isomaltulose.

In a preferred embodiment of the present invention, the rolling compound powder comprises hydrogenated isomaltulose.

In the context of the present invention, the term "hydrogenated isomaltulose" preferably encompasses an isomalt component.

In the context of the present invention, the term "isomalt component" preferably encompasses isomalt, isomalt ST, isomalt GS, an isomalt variant or component thereof. Isomalt is sold under the trademark PALATINIT.

In a preferred embodiment of the present invention, the hydrogenated isomaltulose is selected from the group consisting of 1,1-GPS (1-O-α-D-glucopyranosyl-D-sorbitol), 1,1-GPM (1-O-α-D-glucopyranosyl-D-mannitol), 1,6-GPS (6-O-α-D-glucopyranosyl-D-sorbitol), isomalt, isomalt ST and isomalt GS.

In the context of the present invention, isomalt is a mixture of 1,6-GPS and 1,1-GPM, while isomalt ST is a mixture of 53 to 47% 1,6-GPS and 47 to 53% 1,1-GPM. Isomalt GS is a mixture of 71 to 79% 1,6-GPS and 29 to 21% 1,1-GPM, preferably 75% 1,6-GPS to 25% 1,1-GPM (values given in weight-% on dry matter).

In a further preferred embodiment, it is foreseen to use isomalt variants. In the context of the present invention, isomalt variants are for instance mixtures of 10 to 50% 1,6-GPS, 2 to 20% 1,1-GPS and 30 to 70% 1,1-GPM or mixtures of 5 to 10% 1,6-GPS, 30 to 40% 1,1-GPS and 45 to 60% 1,1-GPM. Isomalt variants may also be in form of 1,6-GPS or 1,1-GPM enriched mixtures. 1,6-GPS enriched mixtures have an 1,6-GPS amount of 58 to 99% and an 1,1-GPM amount of 42 to 1%. 1,1-GPM enriched mixtures have an 1,6-GPS amount of 1 to 42% and an 1,1-GPM amount of 58 to 99% (values given in weight-% on dry matter).

In a further preferred embodiment of the present invention, the isomalt component used is a milled and agglomerated isomalt, in particular a milled and agglomerated isomalt, wherein the milled isomalt particles have a diameter of less than 100 μm, preferably less than 50 μm. Preferably, such a milled and agglomerated isomalt is isomalt DC.

Particle size as described herein is measured by scanning electron microscopy (SEM) or other optical or scanning techniques, for example using a coulter counter.

In a preferred embodiment of the present invention the rolling compound powder comprises essentially hydrogenated isomaltulose.

In a preferred embodiment of the present invention the rolling compound powder consists essentially of hydrogenated isomaltulose.

In a preferred embodiment of the present invention, the rolling compound powder comprises at least 21% by weight, more preferably at least 25% by weight hydrogenated isomaltulose.

In a preferred embodiment of the present invention, the rolling compound powder comprises at least 30% by weight, more preferably at least 40% by weight hydrogenated isomaltulose.

In a preferred embodiment of the present invention, the rolling compound powder comprises at least 50% by weight, more preferably at least 51% by weight hydrogenated isomaltulose.

In a preferred embodiment of the present invention, the rolling compound powder comprises at least 50% by weight and at most 100% by weight hydrogenated isomaltulose. In a preferred embodiment of the present invention, the rolling compound powder comprises at least 50% by weight and at most around 100% by weight hydrogenated isomaltulose. In a preferred embodiment of the present invention, the rolling compound powder comprises at least 50% by weight and at most 99% by weight hydrogenated isomaltulose.

In a preferred embodiment of the present invention, the rolling compound powder comprises at least 70% by weight hydrogenated isomaltulose. In a preferred embodiment of the present invention the rolling compound comprises at least 72% by weight, more preferably at least 73% by weight, even more preferably at least 74% by weight, especially around 75% by weight hydrogenated isomaltulose. The rolling compound powder can also preferably comprise at least 80% by weight, more preferably at least 90% by weight, even more preferably at least 95% by weight hydrogenated isomaltulose. In a preferred embodiment of the present invention the rolling compound powder can comprise at least 99% by weight non-hydrogenated isomaltulose. The rolling compound powder can also comprise around 99% by weight hydrogenated isomaltulose or consist essentially of hydrogenated isomaltulose. The rolling compound powder can also consist of hydrogenated isomaltulose.

In a preferred embodiment of the present invention the rolling compound powder comprises hydrogenated isomaltulose and at least one anti-caking agent. In a preferred embodiment of the present invention the rolling compound powder comprises hydrogenated isomaltulose and an anti-caking agent.

In an alternative embodiment of the present invention the rolling compound powder comprises hydrogenated isomaltulose and comprises no anti-caking agent.

In a preferred embodiment of the present invention 90% by weight, more preferably 99% by weight of the rolling compound powder consists of hydrogenated isomaltulose and an anti-caking agent. In a preferred embodiment of the present invention the rolling compound powder consists essentially of hydrogenated isomaltulose and at least one anti-caking agent.

In a preferred embodiment of the present invention, the anti-caking agent is $SiO_2$ or talcum. In a preferred embodiment of the present invention, the anti-caking agent is $SiO_2$. In a preferred embodiment of the present invention, the anti-caking agent is talcum. In a preferred embodiment of the present invention, the anti-caking agent is $SiO_2$ and talcum.

In a preferred embodiment of the present invention, the rolling compound comprises hydrogenated isomaltulose and $SiO_2$. In a preferred embodiment of the present invention, the rolling compound powder comprises hydrogenated isomaltulose and talcum. In a preferred embodiment of the present invention, the rolling compound powder comprises hydrogenated isomaltulose, $SiO_2$ and talcum.

In a preferred embodiment of the present invention, the rolling compound powder consists of hydrogenated isomaltulose and at least one anti-caking agent. Preferably the anti-caking agent is talcum and/or $SiO_2$. In a preferred embodiment of the present invention, the rolling compound powder consists of hydrogenated isomaltulose and talcum. In a further preferred embodiment of the present invention the rolling compound powder consists of hydrogenated isomaltulose and $SiO_2$. Alternatively, the rolling compound powder can consist of hydrogenated isomaltulose, talcum and $SiO_2$.

In a preferred embodiment of the present invention, the rolling compound powder comprises hydrogenated isomaltulose and around 0.5 to around 5% by weight SiO$_2$. Even more preferred the rolling compound powder comprises hydrogenated isomaltulose and at least 1.5% by weight SiO$_2$. In a preferred embodiment of the present invention, the rolling compound powder comprises hydrogenated isomaltulose and at least 1.5 and at most 5% by weight SiO$_2$.

In a preferred embodiment of the present invention, the rolling compound powder comprises at least 21, more preferably at least 25, even more preferably at least 51% by weight hydrogenated isomaltulose and at least 1.5 and at most 5% by weight SiO$_2$.

In a preferred embodiment of the present invention, the rolling compound powder comprises hydrogenated isomaltulose and at least 5% by weight talcum. In a preferred embodiment of the present invention, the rolling compound powder comprises hydrogenated isomaltulose and at least 20% by weight talcum. In a preferred embodiment of the present invention, the rolling compound powder comprises hydrogenated isomaltulose and at most 60% by weight, more preferably at most 49% by weight talcum.

In an alternative embodiment of the present invention, the rolling compound powder comprises hydrogenated isomaltulose and at least 5 and at most 10% by weight talcum.

In a preferred embodiment of the present invention, the rolling compound powder comprises hydrogenated isomaltulose and at least 20 and at most 49% by weight talcum.

In a preferred embodiment of the present invention, the rolling compound powder comprises hydrogenated isomaltulose, at least 20 to at most 49% by weight talcum and at least 0.5 to at most 5% by weight SiO$_2$.

In a preferred embodiment of the present invention, the rolling compound powder comprises at least 21, more preferably at least 25, even more preferably at least 51% by weight hydrogenated isomaltulose and at most 75, more preferably at most 70, even more preferably at most 49% by weight talcum.

In a preferred embodiment of the present invention, the rolling compound powder comprises non-hydrogenated isomaltulose.

In a preferred embodiment of the present invention the rolling compound powder comprises essentially non-hydrogenated isomaltulose.

In a preferred embodiment of the present invention the rolling compound powder consists essentially of non-hydrogenated isomaltulose.

Non-hydrogenated isomaltulose, also termed isomaltulose, is a disaccharide made from sucrose by the enzymatic rearrangement of the alpha-1,2-linkage between glucose and fructose to an alpha-1,6-linkage.

In a preferred embodiment of the present invention, the rolling compound powder comprises at least 21% by weight, more preferably at least 25% by weight non-hydrogenated isomaltulose.

In a preferred embodiment of the present invention, the rolling compound powder comprises at least 30% by weight, more preferably at least 40% by weight non-hydrogenated isomaltulose.

In a preferred embodiment of the present invention, the rolling compound powder comprises at least 50% by weight, more preferably at least 51% by weight non-hydrogenated isomaltulose.

In a preferred embodiment of the present invention, the rolling compound powder comprises at least 50% by weight and at most 100% by weight non-hydrogenated isomaltulose. In a preferred embodiment of the present invention, the rolling compound powder comprises at least 50% by weight and at most around 100% by weight non-hydrogenated isomaltulose. In a preferred embodiment of the present invention, the rolling compound powder comprises at least 50% by weight and at most 99% by weight non-hydrogenated isomaltulose.

In a preferred embodiment of the present invention, the rolling compound powder comprises at least 70% by weight non-hydrogenated isomaltulose. In a preferred embodiment of the present invention the rolling compound comprises at least 72% by weight, more preferably at least 73% by weight, even more preferably at least 74% by weight, especially around 75% by weight non-hydrogenated isomaltulose. The rolling compound powder can also preferably comprise at least 80% by weight, more preferably at least 90% by weight, even more preferably at least 95% by weight non-hydrogenated isomaltulose. In a preferred embodiment of the present invention the rolling compound powder can comprise at least 99% by weight non-hydrogenated isomaltulose. The rolling compound powder can also comprise around 99% by weight non-hydrogenated isomaltulose or consist essentially of non-hydrogenated isomaltulose. The rolling compound powder can also consist of non-hydrogenated isomaltulose.

In a preferred embodiment of the present invention the rolling compound powder comprises non-hydrogenated isomaltulose and at least one anti-caking agent. In a preferred embodiment of the present invention the rolling compound powder comprises non-hydrogenated isomaltulose and an anti-caking agent.

In an alternative embodiment of the present invention the rolling compound powder comprises non-hydrogenated isomaltulose and comprises no anti-caking agent.

In a preferred embodiment of the present invention the rolling compound powder comprises non-hydrogenated isomaltulose and at least one anti-caking agent. In a preferred embodiment of the present invention the rolling compound powder comprises non-hydrogenated isomaltulose and an anti-caking agent.

In a preferred embodiment of the present invention 90% by weight, more preferably 99% by weight of the rolling compound powder consists of non-hydrogenated isomaltulose and an anti-caking agent. In a preferred embodiment of the present invention the rolling compound powder consists essentially of non-hydrogenated isomaltulose and at least one anti-caking agent.

In a preferred embodiment of the present invention, the anti-caking agent is SiO$_2$ or talcum. In a preferred embodiment of the present invention, the anti-caking agent is SiO$_2$. In a preferred embodiment of the present invention, the anti-caking agent is talcum. In a preferred embodiment of the present invention, the anti-caking agent is SiO$_2$ and talcum.

In a preferred embodiment of the present invention, the rolling compound comprises non-hydrogenated isomaltulose and SiO$_2$. In a preferred embodiment of the present invention, the rolling compound powder comprises non-hydrogenated isomaltulose and talcum. In a preferred embodiment of the present invention, the rolling compound powder comprises non-hydrogenated isomaltulose, SiO$_2$ and talcum.

In a preferred embodiment of the present invention, the rolling compound powder consists of non-hydrogenated isomaltulose and at least one anti-caking agent. Preferably the anti-caking agent is talcum and/or SiO$_2$. In a preferred embodiment of the present invention, the rolling compound powder consists of non-hydrogenated isomaltulose and talcum. In a further preferred embodiment of the present invention the rolling compound powder consists of non-hydrogenated isomaltulose and $SiO_2$. Alternatively, the rolling compound powder can consist of non-hydrogenated isomaltulose, talcum and $SiO_2$.

In a preferred embodiment of the present invention, the rolling compound powder comprises non-hydrogenated isomaltulose and around 0.5 to around 5% by weight $SiO_2$. Even more preferred the rolling compound powder comprises non-hydrogenated isomaltulose and at least 1.5% by weight $SiO_2$. In a preferred embodiment of the present invention, the rolling compound powder comprises non-hydrogenated isomaltulose and at least 1.5 and at most 5% by weight $SiO_2$.

In a preferred embodiment of the present invention, the rolling compound powder comprises at least 21, more preferably at least 25, even more preferably at least 51% by weight non-hydrogenated isomaltulose and at least 1.5 and at most 5% by weight $SiO_2$.

In a preferred embodiment of the present invention, the rolling compound powder comprises non-hydrogenated isomaltulose and at least 5% by weight talcum. In a preferred embodiment of the present invention, the rolling compound powder comprises non-hydrogenated isomaltulose and at least 20% by weight talcum. In a preferred embodiment of the present invention, the rolling compound powder comprises non-hydrogenated isomaltulose and at most 60% by weight, more preferably at most 49% by weight talcum.

In a alternative embodiment of the present invention, the rolling compound powder comprises non-hydrogenated isomaltulose and at least 5 and at most 10% by weight talcum.

In a preferred embodiment of the present invention, the rolling compound powder comprises non-hydrogenated isomaltulose and at least 20 and at most 49% by weight talcum.

In a preferred embodiment of the present invention, the rolling compound powder comprises non-hydrogenated isomaltulose, at least 20 to at most 49% by weight talcum and at least 0.5 to at most 5% by weight $SiO_2$.

In a preferred embodiment of the present invention, the rolling compound powder comprises at least 21, more preferably at least 25, even more preferably at least 51% by weight non-hydrogenated isomaltulose and at most 75, more preferably at most 70, even more preferably at most 49% by weight talcum.

Beside hydrogenated isomaltulose or non-hydrogenated isomaltulose the rolling compound powder can of course comprise further ingredients. In some preferred embodiments of the present invention the rolling compound powder comprising hydrogenated isomaltulose and/or non-hydrogenated isomaltulose does not comprise some specific ingredients.

In a preferred embodiment of the present invention, the rolling compound powder comprises at least one anti-caking agent, more preferably an anti-caking agent. In an alternative embodiment of the present invention, the rolling compound powder comprises essentially no anti-caking agent. In an alternative embodiment of the present invention, the rolling compound powder comprises no anti-caking agent.

In a preferred embodiment of the present invention, the anti-caking agent is $SiO_2$ or talcum. In a preferred embodiment of the present invention, the anti-caking agent is $SiO_2$. In a preferred embodiment of the present invention, the anti-caking agent is talcum. In a preferred embodiment of the present invention, the anti-caking agent is $SiO_2$ and talcum.

In a preferred embodiment of the present invention, the rolling compound powder comprises at least 0.1% by weight and at most 5% by weight $SiO_2$.

In a preferred embodiment of the present invention, the rolling compound powder comprises at least 1.5% by weight and at most 2.5% by weight $SiO_2$.

In a preferred embodiment of the present invention, the rolling compound powder comprises around 2% by weight $SiO_2$.

In an alternative embodiment of the present invention, the rolling compound powder comprises no $SiO_2$.

In an alternative embodiment of the present invention, the rolling compound powder comprises essentially no $SiO_2$.

In a preferred embodiment of the present invention, the rolling compound powder comprises at most 50% by weight talcum, more preferably at most 49% by weight talcum.

In an alternative embodiment of the present invention, the rolling compound powder comprises essentially no talcum.

In an alternative embodiment of the present invention, the rolling compound powder comprises no talcum.

In a preferred embodiment of the present invention, the rolling compound powder comprises starch. In a preferred embodiment of the present invention, the rolling compound powder comprises hydrogenated isomaltulose and starch. In an alternative embodiment of the present invention, the rolling compound powder comprises non-hydrogenated isomaltulose and starch. In a preferred embodiment of the present invention the starch is native starch. In a preferred embodiment of the present invention the starch is rice starch.

In a preferred embodiment of the present invention, the rolling compound powder comprises rice starch. In a preferred embodiment of the present invention, the rolling compound powder comprises hydrogenated isomaltulose and rice starch. In an alternative embodiment of the present invention, the rolling compound powder comprises non-hydrogenated isomaltulose and rice starch.

In a preferred embodiment of the present invention the rice starch is native rice starch. In a preferred embodiment of the present invention the rice starch is raw rice starch. A suitably rice starch is for example Beneo® Remy®, especially Beneo® Remy® FG.

In a preferred embodiment of the present invention, the rolling compound powder comprises at least 1% by weight rice starch. In a preferred embodiment of the present invention, the rolling compound powder comprises at least 10% by weight rice starch. In a preferred embodiment of the present invention, the rolling compound powder comprises at least 20% by weight rice starch. In a preferred embodiment of the present invention, the rolling compound powder comprises at least 30% by weight rice starch. In a preferred embodiment of the present invention, the rolling compound powder comprises at least 40% by weight rice starch.

In a preferred embodiment of the present invention, the rolling compound powder comprises at most 90% by weight rice starch. In a preferred embodiment of the present invention, the rolling compound powder comprises at most 80% by weight rice starch. In a preferred embodiment of the present invention, the rolling compound powder comprises at most 70% by weight rice starch. In a preferred embodiment of the present invention, the rolling compound powder comprises at most 60% by weight rice starch.

In a preferred embodiment of the present invention, the rolling compound powder comprises at least 1% by weight and at most 80% by weight rice starch. In a preferred embodiment of the present invention, the rolling compound powder comprises at least 10% by weight and at most 70% by weight rice starch. In a preferred embodiment of the present invention, the rolling compound powder comprises at least 20% by weight and at most 60% by weight rice starch.

In a preferred embodiment of the present invention, the rolling compound powder comprises at least 30% by weight and at most 70% by weight rice starch and at least 30% by weight and at most 70% by weight hydrogenated isomaltulose. In a preferred embodiment of the present invention, the rolling compound powder comprises at least 30% by weight and at most 70% by weight rice starch and at least 30% by weight and at most 70% by weight non-hydrogenated isomaltulose.

In a preferred embodiment of the present invention, the rolling compound powder comprises at least 40% by weight and at most 60% by weight rice starch and at least 40% by weight and at most 60% by weight hydrogenated isomaltulose. In a preferred embodiment of the present invention, the rolling compound powder comprises at least 40% by weight and at most 60% by weight rice starch and at least 40% by weight and at most 60% by weight non-hydrogenated isomaltulose.

In a preferred embodiment of the present invention, the rolling compound powder consists essentially of at least 40% by weight and at most 60% by weight rice starch and at least 40% by weight and at most 60% by weight hydrogenated isomaltulose. In a preferred embodiment of the present invention, the rolling compound powder consists essentially of at least 40% by weight and at most 60% by weight rice starch and at least 40% by weight and at most 60% by weight non-hydrogenated isomaltulose.

In a preferred embodiment of the present invention, the rolling compound powder consists of at least 40% by weight and at most 60% by weight rice starch and at least 40% by weight and at most 60% by weight hydrogenated isomaltulose. In a preferred embodiment of the present invention, the rolling compound powder consists of at least 40% by weight and at most 60% by weight rice starch and at least 40% by weight and at most 60% by weight non-hydrogenated isomaltulose.

In a preferred embodiment of the present invention, the rolling compound powder consists of at least 45% by weight and at most 55% by weight rice starch and at least 45% by weight and at most 55% by weight hydrogenated isomaltulose. In a preferred embodiment of the present invention, the rolling compound powder consists of at least 45% by weight and at most 55% by weight rice starch and at least 45% by weight and at most 55% by weight non-hydrogenated isomaltulose.

In a preferred embodiment of the present invention, the rolling compound powder comprises essentially no sugar alcohol selected from the group consisting of mannitol, xylitol, sorbitol, erythritol and mixtures thereof. In a preferred embodiment of the present invention, the rolling compound powder comprises at most only traces of a sugar alcohol selected from the group consisting of mannitol, xylitol, sorbitol, erythritol and mixtures thereof.

In a preferred embodiment of the present invention, the rolling compound powder comprises no sugar alcohol selected from the group consisting of mannitol, xylitol, sorbitol, erythritol and mixtures thereof.

In a preferred embodiment of the present invention, the rolling compound powder comprises no mannitol. In a preferred embodiment of the present invention, the rolling compound powder comprises no xylitol. In a preferred embodiment of the present invention, the rolling compound powder comprises no sorbitol. In a preferred embodiment of the present invention, the rolling compound powder comprises no erythritol.

In a preferred embodiment of the present invention, the rolling compound powder comprises at most 39% by weight, more preferably at most 24% by weight a sugar alcohol selected from the group consisting of mannitol, xylitol, sorbitol, erythritol and mixtures thereof.

In a preferred embodiment of the present invention, the rolling compound powder comprises mannitol. In a preferred embodiment of the present invention, the rolling compound powder comprises at most 39% by weight, more preferably at most 24% by weight mannitol.

In a preferred embodiment of the present invention, the rolling compound powder comprises no sugar alcohol selected from the group consisting of xylitol, sorbitol, erythritol and mixtures thereof.

In a preferred embodiment of the present invention, the rolling compound powder is sugar-free. In a further preferred embodiment, the rolling compound is free of sucrose, free of glucose, free of lactose and/or free of fructose or free of combinations of at least two of these sugars.

In a preferred embodiment of the present invention, the rolling compound powder is tooth-friendly.

In a particularly preferred embodiment of the present invention, the hydrogenated or non-hydrogenated isomaltulose is the only sweetening agent present in the rolling compound powder of the present invention. In a preferred embodiment of the present invention, the non-hydrogenated isomaltulose is the only sugar present in the rolling compound of the present invention. In a further preferred embodiment of the present invention, the hydrogenated isomaltulose is the only sugar alcohol present in the rolling compound powder of the present invention. In a further preferred embodiment, the hydrogenated or non-hydrogenated isomaltulose is the only sweetening agent providing a body to the rolling compound powder of the present invention. Thus, in this preferred embodiment, in addition to the hydrogenated or non-hydrogenated isomaltulose, an intense sweetener may also be present in the rolling compound powder.

In a preferred embodiment of the present invention, the non-hydrogenated isomaltulose is essentially the only sugar present in the rolling compound of the present invention. In a further preferred embodiment of the present invention, the hydrogenated isomaltulose is the essentially only sugar alcohol present in the rolling compound powder of the present invention. In a further preferred embodiment, the hydrogenated or non-hydrogenated isomaltulose is the essentially only sweetening agent providing a body to the rolling compound powder of the present invention.

In a preferred embodiment of the present invention, the intense sweetener is selected from the group of cyclamate, saccharin, aspartame, glycyrrhicine, neohesperidine-dihydrochalcone, steveoside, thaumatin, monellin, acesulfame, alitame, sucralose or a mixture thereof.

The present invention solves the underlying technical problem by the provision of a chewing gum product comprising a chewing gum core material wherein a rolling compound powder is applied to the surface of said chewing gum core material and wherein the rolling compound powder comprises hydrogenated or non-hydrogenated isomaltulose. In a preferred embodiment of the present invention the rolling compound powder is a rolling compound powder according to the present invention as it is outlined above.

In a preferred embodiment of the present invention there is thus provided a chewing gum product comprising a chewing gum core material and a rolling compound according to the present invention wherein at least one layer comprising the rolling compound of the present invention is present on the surface of said chewing gum core material.

Accordingly, the chewing gum product according to the present invention comprises a chewing gum core made from a chewing gum core material and a rolling compound powder comprising hydrogenated or non-hydrogenated isomaltulose.

In general, the chewing gum core can be manufactured using the well-known method of manufacturing chewing gum by sequentially combining the various chewing gum ingredients in a commercially available mixer known in the art.

After the ingredients have been thoroughly mixed, the gum mass is discharged from the mixer and shaped into the desired form such as by rolling into sheets and cutting into sticks, extruding into chunks or casting into pellets. Generally, ingredients of the chewing gum core material are mixed by first melting the gum base and adding it into the running mixer. The base may also be melted in the mixer itself. Colour or emulsifiers may also be added at this time. A softener such as glycerine may also be added at this time along with syrup and a portion of bulking agent. Further portions of the bulking agent may then be added to the mixer. A flavouring agent is typically added with a final portion of the bulking agent. The entire mixing procedure typically takes from 5 to 15 minutes, but longer mixing times may sometimes be required. Those skilled in the art will recognise that many variations of the above-described procedure may be followed.

In a preferred embodiment of the present invention, the chewing gum core material is a filled or non-filled chewing gum core material.

In a preferred embodiment of the present invention, the chewing gum core material comprises further at least one additive.

In a preferred embodiment of the present invention, the at least one additive is selected from the group consisting of sugars, preferably tooth-friendly sugars, sugar alcohols, intense sweeteners, hydrocolloid, gum base, plastifiers, lubricant, emulsifiers, protein components, milk components, dairy ingredients, fat and fat substitutes, vegetable fat, vitamins, minerals, pharmaceutically active ingredients, preservatives, aroma, flavourings, such as peppermint, menthol, fruit, strawberry flavour, colours, $TiO_2$, edible acids, such as citric acid, dietary fibres and mixtures thereof.

In a preferred embodiment of the present invention, the chewing gum core material is tooth-friendly. In a preferred embodiment of the present invention, the chewing gum product is tooth-friendly.

In a preferred embodiment of the present invention, the chewing gum core material is sugar-free, in particular free of sucrose, free of glucose, free of lactose and/or free of fructose or free of combinations of at least two of these sugars.

In a preferred embodiment of the present invention, the chewing gum core material comprises at least one tooth-friendly sugar or sugar alcohol.

In a preferred embodiment of the present invention, the at least one tooth-friendly sugar in the chewing gum core material is selected from the group consisting of isomaltulose, nutriose, leukrose and polydextrose. In a preferred embodiment, the sugar is isomaltulose. In a further preferred embodiment, the amount of non-tooth-friendly ingredients is at maximum 1 weight-% (on total weight of the confectionery product).

In a further preferred embodiment of the present invention, the at least one tooth-friendly sugar alcohol in the chewing gum core material is selected from the group of hydrogenated isomaltulose, xylitol, mannitol, maltitol, erythritol, lactitol or sorbitol.

In a further preferred embodiment of the present invention, the only sugar present in the chewing gum core is non-hydrogenated isomaltulose. In a further preferred embodiment of the present invention, the only sugar alcohol present in the chewing gum core is hydrogenated isomaltulose. In a further preferred embodiment of the present invention, the only sugar present in the chewing gum core is non-hydrogenated isomaltulose and the only sugar alcohol present in the chewing gum core is hydrogenated isomaltulose.

The present invention solves the underlying technical problem by the provision of a process for reducing the stickiness of a composition of a chewing gum core material in a chewing gum preparation process, comprising the following steps: a) providing a hydrogenated and/or non-hydrogenated isomaltulose-containing rolling compound powder, b) providing a chewing gum core material and c) applying the rolling compound powder comprising the hydrogenated and/or non-hydrogenated isomaltulose provided in step a) on the surface of the chewing gum core material provided in step b) so as to reduce stickiness of the chewing gum core material to a chewing gum processing machinery. Preferably the rolling compound powder comprises hydrogenated or non-hydrogenated isomaltulose.

In the context of the present invention "chewing gum product" or "chewing gum" refers to the chewing gum core material to/on which the rolling compound powder is applied. When the rolling compound powder is already applied to the chewing gum core material "chewing gum product" or "chewing gum" can also refer to the chewing gum core material together with the rolling compound powder.

In a preferred embodiment the chewing gum core material is provided in step b) as a sheet.

In a preferred embodiment of the present invention the rolling compound powder used in the process is a rolling compound powder according to the present invention as it is outlined above.

The rolling compound powder comprising the hydrogenated or non-hydrogenated isomaltulose can be applied on the surface of the chewing gum core material with techniques known for applying rolling compound powders of the state of the art.

In a preferred embodiment of the present invention the rolling compound powder is applied to the chewing gum core material in a quantity of about 0.5% to about 7%, more preferably of about 1% to about 3% by weight of the resulting chewing gum product.

In a preferred embodiment of the present invention the rolling compound powder is applied to the chewing gum core material in a quantity of at least 0.5% to at most 7%, more preferably of at least 1% to at most 3% by weight of the resulting chewing gum product.

In a preferred embodiment of the present invention the rolling compound powder is applied to the chewing gum core material in a quantity of about 1% to about 15%, more preferably of about 5% to about 10% by weight of the resulting chewing gum product.

In a preferred embodiment of the present invention the rolling compound powder is applied to the chewing gum core material in a quantity of at least 0.5% by weight of the resulting chewing gum product. In a preferred embodiment of the present invention the rolling compound powder is applied to the chewing gum core material in a quantity of at most 15% by weight of the resulting chewing gum product.

In a preferred embodiment of the present invention a rolling compound powder is applied to the chewing gum core material at a level from about 4 to about 65 grams of the rolling compound powder per m² of the surface area of the chewing gum core material. In a preferred embodiment of the present invention a rolling compound powder is applied to the chewing gum core material at a level from about 15 to about 30 grams of the rolling compound powder per m² of the surface area of the chewing gum core material.

The present invention therefore provides chewing gum products comprising a chewing gum core material and a rolling compound powder and processes to obtain them wherein said chewing gum products may be coated or non-coated chewing gum products. Thus, the present invention foresees in one embodiment to provide non-coated chewing gum products such as chewing gum sticks. In another preferred embodiment the present invention foresees to coat the chewing gum product prepared according to the present invention with at least one layer of coating material so as to produce a coated chewing gum product and wherein said at least one layer is enveloping the rolling compound present on the surface of the chewing gum core material.

The present invention solves the underlying technical problem also by the use of hydrogenated or non-hydrogenated isomaltulose in a rolling compound powder for applying to the surface of a chewing gum core material. Preferably a rolling compound according to the present invention as outlined above is used. Preferably a chewing gum core material as outlined above is used.

Further preferred embodiments of the present invention are the subject-matter of the subclaims.

FIG. 1 shows the flowability of various of rolling compound powders according to the present invention compared with rolling compound powders of the state of the art.

The invention is illustrated by way of the following examples and FIG. 1:

EXAMPLE 1: FLOWABILITY OF THE ROLLING COMPOUND ACCORDING TO THE PRESENT INVENTION

The flowability of various rolling compound powders according to the present invention comprising hydrogenated isomaltulose were compared with according rolling compound powders according to the state of the art comprising mannitol. Flowability was measured by using a funnel having a nozzle with a diameter of 15 mm. The flowability was measured as seconds per 100 g rolling compound (s/100 g). The measuring method was performed according to the book Europäisches Arzneibuch, 3$^{rd}$ edition, 1997, pages 150 and 151, point 2.9.16.

The measured flowabilities of the different rolling compound powders are shown in FIG. 1.

Following rolling compound powders were measured:
1: mannitol, fine
2: talc
3: 0.5% SiO$_2$ (Aerosil 200F), 25% talc, 74.5% hydrogenated isomaltulose
4: 25% talc, 75% mannitol
5: 1% SiO$_2$ (Syloid FP), 25% talc, 74% hydrogenated isomaltulose
6: 25% talc, 75% hydrogenated isomaltulose (50% isomalt ST PF+25% isomalt ST C)
7: 0.5% SiO$_2$ (Syloid FP), 25% talc, 74% hydrogenated isomaltulose
8: 25% talc, 70% hydrogenated isomaltulose, 5% rice starch (Remy AX-DR)
9: 25% talc, 70% hydrogenated isomaltulose, 5% rice starch (Remy FG)
10: 25% talc, 74% hydrogenated isomaltulose, 1% rice starch (Remy AX-DR)
11: 25% talc, 74% hydrogenated isomaltulose, 1% rice starch (Remy FG)
12: 1% SiO$_2$ (Aerosil 200F), 99% hydrogenated isomaltulose
13: 2% SiO$_2$ (Syloid FP), 25% talc, 73% hydrogenated isomaltulose
14: 95% hydrogenated isomaltulose, 5% rice starch (Remy AX-DR)
15: 25% talc, 75% rice starch (Remy AX-DR)
16: 25% talc, 75% hydrogenated isomaltulose (isomalt ST PF)
17: 100% hydrogenated isomaltulose (80% isomalt ST PF+20% isomalt ST C)
18: 2% SiO$_2$ (Aerosil 200F), 25% talc, 73% hydrogenated isomaltulose
19: 100% hydrogenated isomaltulose (80% isomalt ST PF+20% isomalt DC 100)
20: 100% hydrogenated isomaltulose (isomalt ST PF)
21: 100% rice starch
22: 2% SiO$_2$ (Aerosil 200F), 98% rice starch
23: 2% SiO$_2$ (Aerosil 200F), 98% mannitol
24: 2% SiO$_2$ (Aerosil 200F), 98% hydrogenated isomaltulose Pure mannitol shows no flowability at all. A rolling compound powder consisting of 75% hydrogenated isomaltulose and 25% talcum shows a much better flowability than a rolling compound powder consisting of 75% mannitol and 25% talcum. The best flowability was found for a rolling compound powder consisting of 98% hydrogenated isomaltulose and 2% SiO$_2$.

EXAMPLE 2: ADHESION TO THE MACHINERY

A rolling compound powder consisting of 55% hydrogenated isomaltulose and 45% talcum was applied to the surface of sheets of a conventional chewing gum core material.

The use of the rolling compound powder consisting of 55% hydrogenated isomaltulose and 45% talcum showed a good prevention of adhesion to the used machinery such as rolling machines and scoring machines having steel surfaces and other polished surfaces and also such as conveyor belts having teflon or plastic surfaces.

Accordingly, the rolling compound powder according to the present invention is a good release agent to prevent the adhesion of a chewing gum core material during the processing steps after forming the chewing gum core.

The invention claimed is:
1. A rolling compound powder for applying to the surface of a chewing gum core material, the rolling compound powder comprising at least 70% by weight hydrogenated isomaltulose particles having a diameter of less than 50 μm and at least 1.5% by weight and at most 5% by weight SiO$_2$.

2. The rolling compound powder according to claim 1, comprising around 2% by weight $SiO_2$.

3. The rolling compound powder according to claim 1, comprising no talcum.

4. The rolling compound powder according to claim 1, comprising no sugar alcohol selected from the group consisting of mannitol, xylitol, sorbitol, erythritol and mixtures thereof.

5. The rolling compound powder according to claim 1 in combination with a chewing gum core material, wherein a layer comprising the rolling compound is present on a surface of the chewing gum core material.

6. The rolling compound powder according to claim 5, comprising at least 80% by weight hydrogenated isomaltulose.

7. The rolling compound powder according to claim 5, comprising around 2% by weight $SiO_2$.

8. The rolling compound powder according to claim 5, comprising no talcum.

9. The rolling compound powder according to claim 5, comprising no sugar alcohol selected from the group consisting of mannitol, xylitol, sorbitol, erythritol and mixtures thereof.

10. A rolling compound powder for applying to the surface of a chewing gum core material, the rolling compound powder comprising at least 70% by weight hydrogenated isomaltulose particles having a diameter of less than 50 μm and an anti-caking agent, wherein the rolling compound powder comprises essentially no sugar alcohol selected from the group consisting of mannitol, xylitol, sorbitol, erythritol, and mixtures thereof.

11. The rolling compound powder according to claim 10, wherein the rolling compound powder includes hydrogenated isomaltulose at a concentration of at least 90% by weight of the rolling compound powder.

12. The rolling compound powder according to claim 10, wherein the anti-caking agent is $SiO_2$ or talcum.

13. The rolling compound powder according to claim 12, wherein the rolling compound powder comprises hydrogenated isomaltulose and at least 5% by weight talcum.

14. The rolling compound powder according to claim 12, wherein the rolling compound powder comprises hydrogenated isomaltulose and at least 0.5% by weight $SiO_2$.

15. The rolling compound powder according to claim 10, wherein the anti-caking agent is $SiO_2$ and the rolling compound powder consists essentially of 98% by weight hydrogenated isomaltulose and 2% $SiO_2$.

16. The rolling compound powder according to claim 1, wherein the hydrogenated isomaltulose is the only sweetening agent present in the rolling compound.

17. The rolling compound powder according to claim 10, wherein the hydrogenated isomaltulose is the only sweetening agent present in the rolling compound.

18. The rolling compound powder according to claim 1, consisting of 98% by weight hydrogenated isomaltulose particles having a diameter of less than 50 μm and 2% by weight $SiO_2$.

19. The rolling compound powder according to claim 1, wherein the rolling compound powder is configured to reduce sticking of chewing gum core materials to processing machinery.

* * * * *